United States Patent
Chen et al.

(10) Patent No.: US 8,326,054 B2
(45) Date of Patent: Dec. 4, 2012

(54) METHOD FOR PRIOR IMAGE CONSTRAINED IMAGE RECONSTRUCTION IN CARDIAC CONE BEAM COMPUTED TOMOGRAPHY

(75) Inventors: Guang-Hong Chen, Madison, WI (US); Jie Tang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 564 days.

(21) Appl. No.: 12/626,366

(22) Filed: Nov. 25, 2009

(65) Prior Publication Data

US 2010/0128958 A1   May 27, 2010

Related U.S. Application Data

(60) Provisional application No. 61/118,314, filed on Nov. 26, 2008.

(51) Int. Cl.
  *G06K 9/36* (2006.01)
  *G06K 9/00* (2006.01)
(52) U.S. Cl. ............ 382/232; 382/131; 382/132; 378/4; 378/8
(58) Field of Classification Search .............. 382/131, 382/132, 232; 378/4, 8
  See application file for complete search history.

(56) References Cited

U.S. PATENT DOCUMENTS

| | | | |
|---|---|---|---|
| 4,878,169 A | 10/1989 | Toner et al. | |
| 6,841,998 B1 | 1/2005 | Griswold | |
| 7,289,049 B1 | 10/2007 | Fudge et al. | |
| 7,330,027 B2 | 2/2008 | Kozerke et al. | |
| 7,358,730 B2 | 4/2008 | Mistretta et al. | |
| 7,408,347 B2 | 8/2008 | Mistretta et al. | |
| 7,519,412 B2 | 4/2009 | Mistretta | |
| 7,545,901 B2 | 6/2009 | Mistretta | |
| 7,558,414 B2 | 7/2009 | Griswold | |
| 7,646,924 B2 | 1/2010 | Donoho | |
| 7,647,088 B2 | 1/2010 | Mistretta et al. | |
| 7,916,828 B1 * | 3/2011 | Khare et al. | 378/4 |
| 2006/0109952 A1 | 5/2006 | Chen | |
| 2007/0010731 A1 | 1/2007 | Mistretta | |
| 2007/0038073 A1 | 2/2007 | Mistretta | |
| 2007/0106149 A1 | 5/2007 | Mistretta | |
| 2007/0156044 A1 | 7/2007 | Mistretta et al. | |
| 2007/0167707 A1 | 7/2007 | Mistretta et al. | |
| 2007/0167728 A1 | 7/2007 | Mistretta et al. | |

(Continued)

OTHER PUBLICATIONS

Candes, et al., Robust Uncertainty Principles: Exact Signal Reconstruction from Highly Incomplete Frequency Information, IEEE Transactions on Information Theory, vol. 52, No. 2, Feb. 2006, 489-509.

(Continued)

*Primary Examiner* — Alexander H Taningco
(74) *Attorney, Agent, or Firm* — Quarles & Brady, LLP

(57) ABSTRACT

An image reconstruction method for cardiac cone beam CT is provided, in which data acquired as truncated projections using current cardiac flat panel detectors is reconstructed to form a high quality image of a desired cardiac phase. An iterative method is utilized to reconstruct a prior image from all of the acquired truncated data without cardiac gating. Subsequently, a reconstruction method, in which the prior image is utilized in a prior image constrained reconstruction method, is utilized to reconstruct images for each individual cardiac phase. The objective function in such a prior image constrained reconstruction method is modified to incorporate the conditions used in the production of the prior image so that the data truncation problem is properly addressed.

17 Claims, 12 Drawing Sheets

U.S. PATENT DOCUMENTS

| | | | |
|---|---|---|---|
| 2007/0167729 | A1 | 7/2007 | Mistretta et al. |
| 2008/0199063 | A1* | 8/2008 | O'Halloran et al. ........... 382/131 |
| 2008/0219535 | A1 | 9/2008 | Mistretta et al. |
| 2008/0292163 | A1* | 11/2008 | DiBella et al. ................. 382/131 |
| 2009/0076369 | A1 | 3/2009 | Mistretta |
| 2009/0129651 | A1 | 5/2009 | Zagzebski et al. |
| 2009/0161932 | A1* | 6/2009 | Chen ............................. 382/131 |
| 2009/0161933 | A1* | 6/2009 | Chen ............................. 382/131 |
| 2009/0175523 | A1* | 7/2009 | Chen et al. .................... 382/130 |
| 2009/0262996 | A1* | 10/2009 | Samsonov et al. ............ 382/130 |
| 2009/0274355 | A1* | 11/2009 | Chen et al. .................... 382/131 |

OTHER PUBLICATIONS

Donoho, Compressed Sensing, Sep. 14, 2004, pp. 1-34.

Donoho, Compressed Sensing, IEEE Transactions on Information Theory, vol. 52, No. 4, Apr. 2006, 1289-1306.

Fessler, et al., Iterative Image Reconstruction in MRI With Separate Magnitude and Phase Regularization, IEEE International Symposium on Biomedical Imaging: Nano to Macro, 2004; 1:209-212.

Lustig, et al., Rapid MR Imaging with 'Compressed Sensing' and Randomly Under-Sampled 3DFT Trajectories, Proc. Intl. Soc. Mag. Reson. Med. 14 (2006), p. 695.

Lustig, Student Member, IEEE, Compressed Sensing MRI, 18 pages, 2007.

Lustig, et al., Sparse MRI: The Application of Compressed Sensing for Rapid MR Imaging, Magnetic Resonance in Medicine 58:1182-1195 (2007).

Mistretta, et al., Highly Constrained Backprojection for Time-Resolved MRI, Magn Reson Med, 2006, 55(1):30-40.

O'Halloran, et al., Iterative Projection Reconstruction of Time-Resolved Images Using Highly-Constrained Back-Projection (HYPR), Magn Reson Med, 2008, 59:132-139 (published online Dec. 3, 2007).

Schmidt, Least Squares Optimization with L1-Norm Regularization, Dec. 2005, pp. 1-12.

Song, et al., Sparseness Prior Based Iterative Image Reconstruction for Retrospectively Gated Cardiac Micro-CT, Med. Phys. 34(11), Nov. 2007, pp. 4476-4483.

Chen Guang-Hong et al: Prior Image Constrained Compressed Sensing (PICCS): A Method to Accurately Reconstruct Dynamic CT Images From Highly Undersampled Projection Data Sets; Medical Physics, AIP, Melville, NY US; vol. 35, No. 2, Jan. 28, 2008, pp. 660-663.

Brian Nett et al: Tomosynthesis Via Total Variation Minimization Reconstruction and Prior Image Constrained Compressed Sensing (PICCS) on A C-Arm System; vol. 6913; Mar. 18, 2008; pp. 1-6.

Yu et al: Region of Interest Reconstruction From Truncated Data in Circular Cone-Beam CT; IEEE Transactions on Medical Imaging, IEEE Service Center, Piscataway, NJ US; vol. 25, No. 7; Jul. 1, 2006; p. 869-p. 872.

Chen Guang-Hong et al: Image Reconstruction for Fan Beam Differential Phase Contrast Computed Tomography; Physics in Medicine and Biology, Taylor and Francis LTD, London GB, vol. 53, No. 4; Feb. 21, 2008; p. 1018, 1019, 1024.

PCT/US2009/065920; PCT International Search Report and Written Opinion.

* cited by examiner

METHOD FOR PRIOR IMAGE CONSTRAINED IMAGE RECONSTRUCTION IN CARDIAC CONE BEAM COMPUTED TOMOGRAPHY

CROSS-REFERENCE TO RELATED APPLICATIONS

This application claims the benefit of U.S. Provisional Patent Application Ser. No. 61/118,314 filed on Nov. 26, 2008, and entitled "Method for Prior Image Constrained Image Reconstruction in Cardiac Cone Beam Computed Tomography."

STATEMENT REGARDING FEDERALLY SPONSORED RESEARCH

This invention was made with United States government support awarded by the following agency: NIH EB005712 and EB007021. The United States government has certain rights in this invention.

BACKGROUND OF THE INVENTION

The field of the invention is medical imaging and particularly, methods for reconstructing images from acquired image data.

In a computed tomography system, an x-ray source projects a fan-shaped beam which is collimated to lie within an x-y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," "attenuation profile," or "projection."

The source and detector array in a conventional CT system are rotated on a gantry within the imaging plane and around the object so that the angle at which the x-ray beam intersects the object constantly changes. The transmission profile from the detector array at a given angle is referred to as a "view," or "projection," and a "scan" of the object comprises a set of views made at different angular orientations during one revolution of the x-ray source and detector. In a "cone beam" arrangement, the focal spot of the x-ray source and the detector define a cone-shaped beam of x-rays. When a subject is not fully covered by the cone beam, the views contained therein are said to be "truncated." The degree of this truncation depends on factors including the size of the detector utilized, the size of the subject, and the view angle. When the subject is a human body, measuring non-truncated cone beam projections requires an impracticably large detector. Thus, in medical applications, the measured cone beam projections are typically always truncated.

In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units," which are used to control the brightness of a corresponding pixel on a display. The filtered backprojection image reconstruction method is the most common technique used to reconstruct CT images from acquired transmission profiles.

According to standard image reconstruction theories, in order to reconstruct an image without aliasing artifacts, the sampling rate employed to acquire image data must satisfy the so-called Nyquist criterion, which is set forth in the Nyquist-Shannon sampling theorem. Moreover, in standard image reconstruction theories, no specific prior information about the image is needed. On the other hand, when some prior information about the desired image is available and appropriately incorporated into the image reconstruction procedure, an image can be accurately reconstructed even if the Nyquist criterion is violated. For example, if one knows a desired image is circularly symmetric and spatially uniform, only one view of parallel-beam projections (i.e., one projection view) is needed to accurately reconstruct the linear attenuation coefficient of the object. As another example, if one knows that a desired image consists of only a single point, then only two orthogonal projections that intersect at the point are needed to accurately reconstruct an image of the point. Thus, if prior information is known about the desired image, such as if the desired image is a set of sparsely distributed points, it can be reconstructed from a set of data that was acquired in a manner that does not satisfy the Nyquist criterion. Put more generally, knowledge about the sparsity of the desired image can be employed to relax the Nyquist criterion; however, it is a highly nontrivial task to generalize these arguments to formulate a rigorous image reconstruction theory.

Recently, a new mathematical framework for data processing termed "compressed sensing" (CS) has been formulated. Using compressed sensing, only a small set of linear projections of a sparse image are required to reconstruct a quality image. The theory of CS is described by E. Candès, J. Romberg, and T. Tao, in "Robust uncertainty principles: Exact Signal Reconstruction from Highly Incomplete Frequency Information," *IEEE Transactions on Information Theory* 2006; 52:489-509, and by D. Donoho in "Compressed Sensing," *IEEE Transactions on Information Theory* 2006; 52:1289-1306, and is disclosed, for example, in U.S. patent application Ser. No. 11/199,675.

Although the mathematical framework of CS is elegant, the applicability of CS to a reconstruction method in the field of medical imaging critically relies on the medical images being sparse. Unfortunately, a medical image is often not sparse in the standard pixel representation. Despite this, mathematical transforms can be applied to a single image in order to sparsify the image. Such transforms are thus referred to as "sparsifying transforms." More specifically, given a sparsifying transform, $\Psi$, CS image reconstruction can be implemented by minimizing the following objective function:

$$\|\Psi I\|_1 \text{ such that } AI = Y \quad \text{Eqn. (1).}$$

In the above objective function, I is a vector that represents the desired image, Y is a vector that represents the data acquired by the imaging system, A is a system matrix that describes the measurements, and the following:

$$\|x\|_1 = \sum_{i=1}^{N} |x_i|; \quad \text{Eqn. (2)}$$

is the so-called $L_1$-norm of an N-dimensional vector, X. Namely, CS image reconstruction determines an image that minimizes the $L_1$-norm of the sparsified image among all images that are consistent with the physical measurements, $AI=Y$.

The basic ideas in the CS image reconstruction theory can be summarized as follows. Instead of directly reconstructing a desired image in pixel representation, a sparsified version of the desired image is reconstructed. In the sparsified image, substantially fewer image pixels have significant image values; thus, it is possible to reconstruct the sparsified image from an undersampled data set. After the sparsified desired image is reconstructed, an "inverse sparsifying transform" is used to transform the sparsified image back to the desired image. In practice, there is no need to have an explicit form for the "inverse" sparsifying transform. In fact, only the sparsifying transform is needed in image reconstruction.

In practical interventional cardiology, a C-arm system with a small flat-panel detector is used. For example, the panel size is typically only about 20 cm by 20 cm, which provides a field-of-view on the order of only 12 cm. For x-ray projection imaging, this field-of-view is barely sufficient to cover the entire heart. Moreover, each cone beam projection acquired using such a C-arm system is truncated. Even without ECG gating, filtered backprojection reconstruction algorithms can not generally reconstruct a satisfactory image. In fact, it is inherently difficult to reconstruct an image in this situation, provided that no a priori information is available. Therefore, it is even a tremendous challenge to produce a suitable prior image for use in image reconstruction methods, such as prior image constrained compressed sensing ("PICCS") methods as applied to cardiac imaging.

SUMMARY OF THE INVENTION

The present invention overcomes the aforementioned drawbacks by providing a method for producing a prior image from truncated cone beam projection data, such that quality images can be reconstructed using an image reconstruction method such as prior image constrained compressed sensing ("PICCS") for cardiac applications.

The present invention provides an image reconstruction method applicable to cardiac cone-beam x-ray computed tomography ("CT"). More specifically, the present invention provides an image reconstruction method that reconstructs a high quality image of a selected cardiac phase from a set of truncated cone beam image data.

It is one aspect of the present invention to provide an image reconstruction method that enables cardiac cone beam CT using current cardiac flat panel detectors in which data is acquired as truncated projections. In general, this method includes an iterative method that is utilized to reconstruct a prior image from all of the acquired truncated data without cardiac gating and a reconstruction method, in which the prior image is utilized in a prior image constrained reconstruction method, that reconstructs images for each individual cardiac phase. The objective function in such a prior image constrained reconstruction method is modified to incorporate the conditions used in the production of the prior image so that the data truncation problem is properly addressed.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
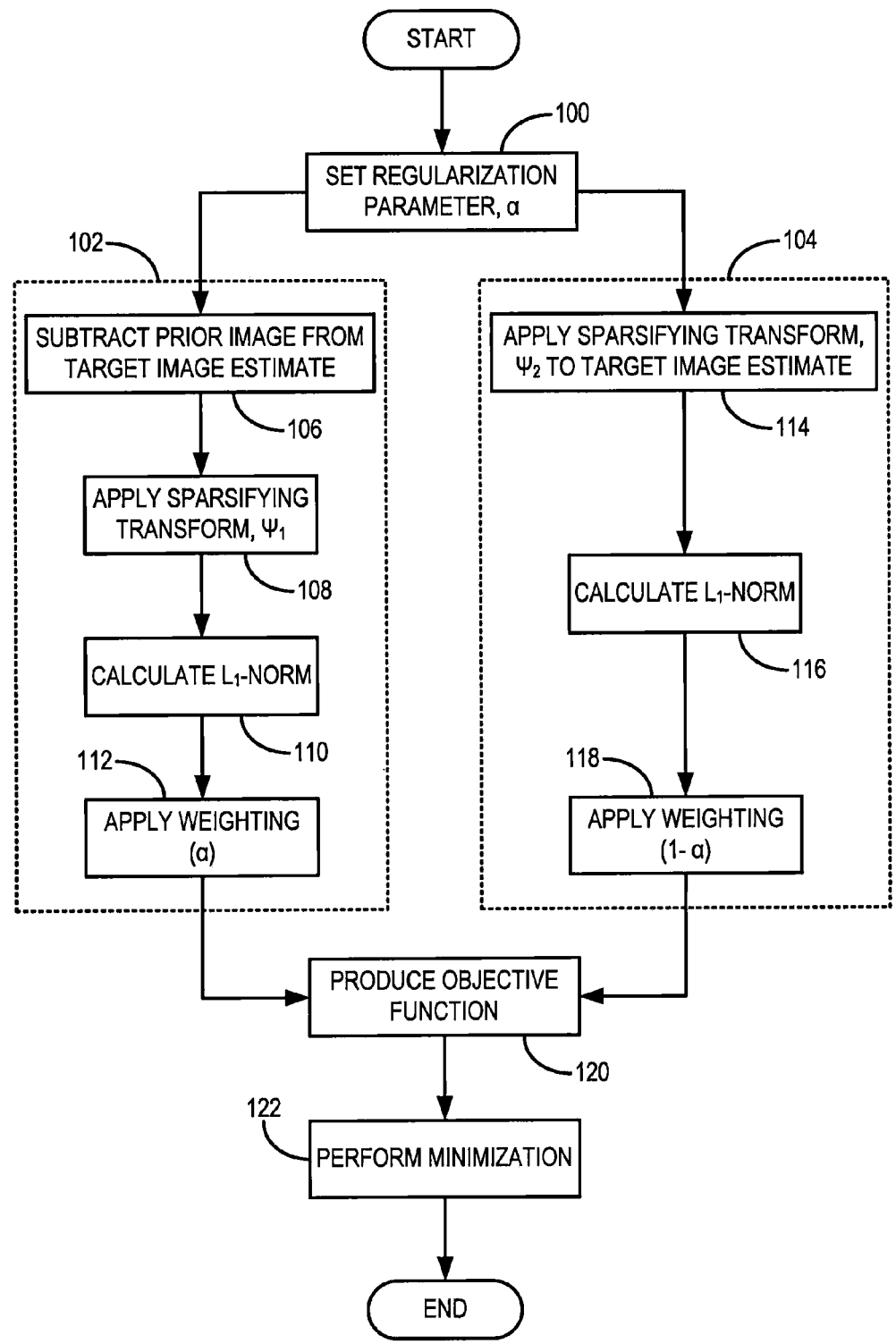
FIG. 1 is a flowchart setting forth the steps of an exemplary prior image constrained compressed sensing ("PICCS") image reconstruction method employed when practicing the present invention.

Generally speaking, the method of reconstructing an image from a set of data includes a series of numerical steps to estimate a desired image, I, from the measured data samples, Y. More specifically, the image reconstruction should fulfill the following consistency condition:

$$AI=Y \qquad \text{Eqn. (3);}$$

where A is a system matrix. In general, the system matrix, A, can be viewed as a forward projection operator that relates the desired image, I, to the acquired data samples, Y. When dealing with computed tomography ("CT") imaging, the system matrix can include a reprojection operation, while in magnetic resonance imaging ("MRI"), it can include a Fourier transform operation. The consistency condition of Eqn. (3), put in other words, states that when an image is faithfully reconstructed, the forward operation should substantially mimic the actual data acquisition procedure in order to generate a correct estimate of the measured projection data.

Turning now to the method of the present invention, a method for reconstructing a quality desired image is provided. In general, a "prior image" is employed to constrain an iterative image reconstruction method, in which the principles of compressed sensing ("CS") are utilized. For example, in addition to the sparsifying transforms commonly used in CS, an image is further sparsified by subtracting the prior image from the desired image. As a result, an image can be accurately reconstructed using a substantially fewer number of samples than required by CS methods.

More specifically, given a prior image, $I_P$, and a desired image to be reconstructed, $I$, the method of the present invention for image reconstruction is implemented by minimizing the following objective function:

$$\alpha\|\Psi_1(I-I_P)\|_1+(1-\alpha)\|\Psi_2 I\|_1 \qquad \text{Eqn. (4)}$$

where $\Psi_1$ and $\Psi_2$ are sparsifying transforms, $\|\ldots\|_1$ is an $L_1$-norm operation, and $\alpha$ is a regularization parameter that is utilized to control the relative weight of the two terms in the objective function of Eqn. (4). As noted above, $$\|x\|_1 = \sum_{i=1}^{N}|x_i|; \qquad \text{Eqn. (5)}$$

indicates the $L_1$-norm of an N-dimensional vector, x. More generally, a deviation from the true $L_1$-norm is possible while still maintaining adequate image quality in the desired image. For example, the objective function of Eqn. (4) can be generalized as:

$$\alpha\|\Psi_1(I-I_P)\|_p+(1-\alpha)\|\Psi_2 I\|_p, \qquad \text{Eqn. (6)}$$

where $\|\ldots\|_p$ is an $L_p$-norm operation having the form:

$$\|x\|_p = \left(\sum_{i=1}^{N}|x_i|^p\right)^{1/p}. \qquad \text{Eqn. (7)}$$

As noted above, preferably p=1.0; however, in the alternative, different values of p are possible. It should be appreciated by those skilled in the art that the further the value of p deviates from p=1.0, generally, the more degradation will be evident in the reconstructed desired image.

The sparsifying transforms in Eqn. (4), $\Psi_1$ and $\Psi_2$, are, in general, different; however, in the alternative, $\Psi_1$ and $\Psi_2$ may be the same sparsifying transform. Exemplary sparsifying transforms include a wavelet transform, a first order finite difference, a second order finite difference, and a discrete gradient transform, such as, for example, a discrete gradient transform, $\nabla_{m,n}$, having the following form:

$$\nabla_{m,n}I(m,n) = \sqrt{\begin{array}{l}[I(m+1,n)-I(m,n)]^2+\\ [I(m,n+1)-I(m,n)]^2\end{array}}; \qquad \text{Eqn. (8)}$$

where the indices m and n indicate the location of a pixel in an image, I. The image specified as $\nabla_{m,n}I(m,n)$ is commonly referred to as the "gradient image."

Both of the terms in the objective function of Eqn. (4) are important. As a result of their importance, the selection of the regularization parameter, $\alpha$, is utilized to control the overall image reconstruction process. Therefore, the selection of the regularization parameter, $\alpha$, will depend on the choice of the prior image, $I_P$, and also the clinical application at hand. For example, the second term in the objective function of Eqn. (4), $(1-\alpha)\|\Psi_2 I\|_1$, mitigates streaking artifacts that are potentially inherited from the prior image, $I_P$. For further example, selecting a regularization parameter of $\alpha \approx 0.3$-$0.7$ is generally sufficient for cardiac imaging applications.

To better incorporate the consistency condition of Eqn. (3) into the overall image reconstruction, the method of Lagrange multipliers is utilized. In such a manner, the consistency condition is employed to add a further constraint on the minimization of the objective function set forth in Eqn. (4). A new objective function is thus produced, which has the form:

$$\alpha\|\Psi_1(I-I_P)\|_1+(1-\alpha)\|\Psi_2 I\|_1+\lambda\|X\|_2^2 \qquad \text{Eqn. (9)}$$

where $\lambda$ is the Lagrange multiplier, x is a difference matrix, and $\|\ldots\|_2^2$ is a squared $L_2$-norm operation, which, for an N-dimensional vector, x, has the form:

$$\|x\|_2^2 = \sum_{i=1}^{N}x_i^2. \qquad \text{Eqn. (10)}$$

The difference matrix in Eqn. (9) accounts for the consistency condition of Eqn. (3), and has the following form:

$$X = AI - Y \qquad \text{Eqn. (11)}.$$

The Lagrange multiplier, $\lambda$, is determined empirically for the particular imaging system employed when practicing the present invention. For example, the Lagrange multiplier, $\lambda$, is determined by a pre-determined tradeoff between the desired data consistency requirement and the similarity to the prior image, $I_P$. When a large Lagrange multiplier, $\lambda$, is selected, the reconstructed image has lower noise variance; however, this may be achieved as a loss of the high spatial resolution characteristic of the prior image. Similarly, when a smaller Lagrange multiplier, $\lambda$, is used, the high spatial resolution characteristic of the prior image is well preserved, but the noise variance can be high in the desired image. Such a situation affects the contrast-to-noise ratio achievable by the imaging system utilized.

The objective function presented in Eqn. (9) can further be altered in order to account for noise of the imaging system. In such a manner, the following objective function is minimized:

$$\alpha\|\Psi_1(I-I_P)+(1-\alpha)+\|\Psi_2 I\|_1+\lambda(X^T DX) \qquad \text{Eqn. (12)};$$

where $X^T$ is the transpose of the difference matrix, X, and D is a system noise matrix, which is a diagonal matrix having the following matrix elements:

$$D_{ij} = \begin{cases} \dfrac{1}{\sigma_n^2} & \text{if } i = j \\ 0 & \text{if } i \neq j, \end{cases}; \qquad \text{Eqn. (13)}$$

where $\sigma_n^2$ is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. Alternatively, in an MR imaging system, the noise parameter, $\sigma_n^2$, is estimated noise variance in the $n^{th}$ receiver coil.

In the method of the present invention, the prior image, $I_P$, plays several roles. For example, it serves as a seed image in the iterative reconstruction, which accelerates the overall image reconstruction method. In addition, the prior image, $I_P$, is employed to further sparsify the desired image, I, and, thus, serves as yet another sparsifying transform. Moreover, when the signal-to-noise ratio ("SNR") is relatively high in the prior image, $I_P$, then the final reconstructed image will inherit this high SNR. As referred to herein, a prior image, $I_P$, is an image of the subject that includes a priori information indicative of the desired image to be reconstructed. The prior image, $I_P$, can be from a previously performed imaging study, or can be reconstructed from image data acquired in the same session as the image data acquired for the desired images. Typically, the prior image, $I_P$, is acquired using the same imaging modality as the desired images; however, there are applications where the prior image, $I_P$, can be obtained from a different imaging modality than the desired images.

With reference now to FIG. 1, one implementation of the method of the present invention employs the objective function of Eqn. (4), and begins by initializing the regularization parameter, α, as indicated at step 100. The choice of the regularization parameter, α, determines the trade-off between the sparsity of the desired image, and the influence of the prior image on the desired image. Accordingly, the value of the regularization parameter, α, will vary depending on the clinical application at hand. For example, a value of α≈0.3-0.7 is generally sufficient for cardiac imaging applications. Subsequently, the first and second terms in the objective function of Eqn. (4) are initialized, as indicated in steps 102 and 104, respectively. The initialization of the first term, $\alpha \|\Psi_1(I-I_P)\|_1$, begins at step 106 where the prior image, $I_P$, is subtracted from an estimate of the desired image, I, to produce a "difference image." The particular choice of the prior image, $I_P$, and the estimate of the desired image, I, will depend on the imaging modality and the particular clinical application. Accordingly, different alternatives for these choices will be discussed in detail below. The difference image is subsequently sparsified by applying the sparsifying transform, $\Psi_1$, as indicated at step 108. As described above, the sparsifying transform, $\Psi_1$, can be any number of mathematical operations, including a wavelet transform, a first order finite difference, a second order finite difference, and a discrete gradient transform. The $L_1$-norm of this sparsified difference image is then calculated at step 110. The result of this process is then weighted by the regularization parameter, α, as indicated at step 112.

The initialization of the second term in the objective function of Eqn. (4), $(1-\alpha)\|\Psi_2 I\|_1$, begins at step 114 where the estimate of the desired image, I, is sparsified through the application of the sparsifying transform, $\Psi_2$. Subsequently, the $L_1$-norm of this sparsified desired image estimate is calculated at step 116. When the discrete gradient transform, $\nabla_{m,n}$, is selected as the sparsifying transform, $\Psi_2$, steps 114 and 116 can be viewed as calculating the total variation, TV, of the desired image estimate, which has the form:

$$TV(I) = \|\nabla I\|_1 = \Sigma |\nabla I| \qquad \text{Eqn. (14).}$$

After the $L_1$-norm of the sparsified desired image estimate is calculated, the result is weighted by (1−α), as indicated at step 118. The objective function of Eqn. (4) is subsequently produced in step 120 by adding the first and second terms together. This objective function is then minimized, as indicated at step 122, using, for example, a nonlinear conjugate gradient method. The minimization process proceeds until a stopping criterion is satisfied. The stopping criterion includes, for example, comparing the current estimate of the desired image with the estimate of the desired image from the previous iteration. Such a stopping criterion has the following form:

$$\sum_i \sum_j (I_{ij}^{(k+1)} - I_{ij}^{(k)})^2 < \varepsilon; \qquad \text{Eqn. (15)}$$

where, $I_{ij}^{(k+1)}$ is the value of the $(k+1)^{th}$ estimate of the desired image at the pixel location (i,j); $I_{ij}^{(k)}$ is the value of the $k^{th}$ estimate of the desired image at the pixel location (i,j); and ε is a preset tolerance of the accuracy of the image reconstruction process.

Figure 2:
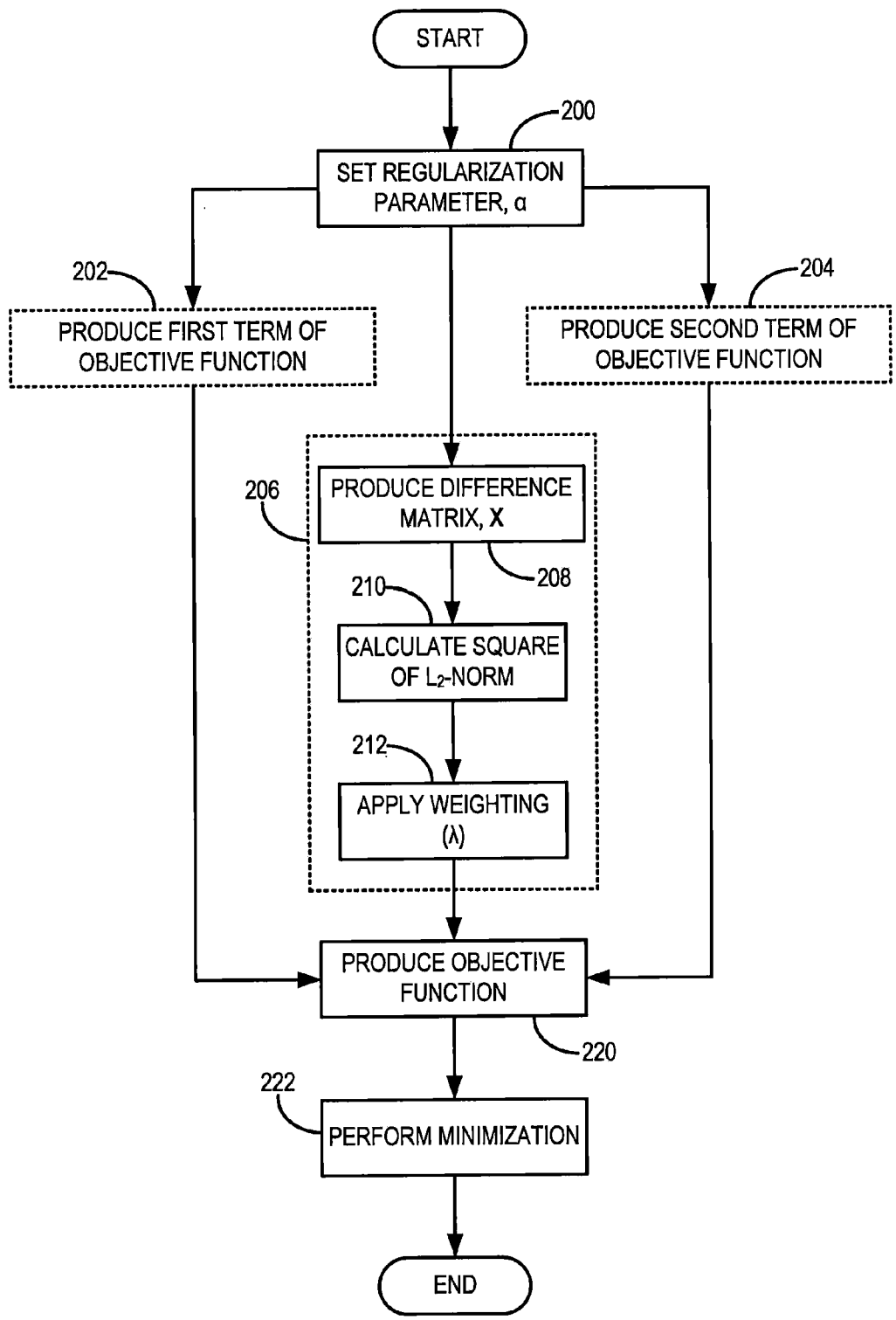
FIG. 2 is a flowchart setting forth the steps of another exemplary prior image constrained compressed sensing ("PICCS") image reconstruction method employed when practicing the present invention.

With reference now to FIG. 2, another implementation of the method of the present invention employs the objective function of Eqn. (9), and begins by initializing the regularization parameter, α, as indicated at step 200. Subsequently, the first and second terms in the objective function of Eqn. (9) are initialized, as indicated in steps 202 and 204, respectively. This process proceeds in the same manner as described above with reference to steps 102 and 104 in FIG. 1. Now, however, the consistency condition of Eqn. (3) is incorporated into a third term, $\lambda \|X\|_2^2$, which is initialized at step 206. First, the difference matrix, X, is produced, as indicated at step 208. As described above in detail, the difference matrix, X, corresponds to the consistency condition of Eqn. (3) and has the following form:

$$X = AI - Y \qquad \text{Eqn. (16).}$$

Thus, the difference matrix is determined by applying the system matrix, A, to the estimate of the desired image, I, and subsequently subtracting the acquired image data, Y, that corresponds to the desired image. The square of the $L_2$-norm of the difference matrix, X, is calculated next at step 210. After the square of the $L_2$-norm of the difference matrix, X, has been produced, the Lagrange multiplier, λ, is determined and employed to weight the difference matrix, X, as indicated at step 212. As described above, the Lagrange multiplier is empirically determined, and the value selected, by the user based on the clinical application at hand. The objective function of Eqn. (9) is subsequently produced in step 220 by adding the first, second, and third terms together. This objective function is then minimized, as indicated at step 222, using, for example, a nonlinear conjugate gradient method. The minimization process proceeds until a stopping criterion is satisfied, as described above.

Figure 3:
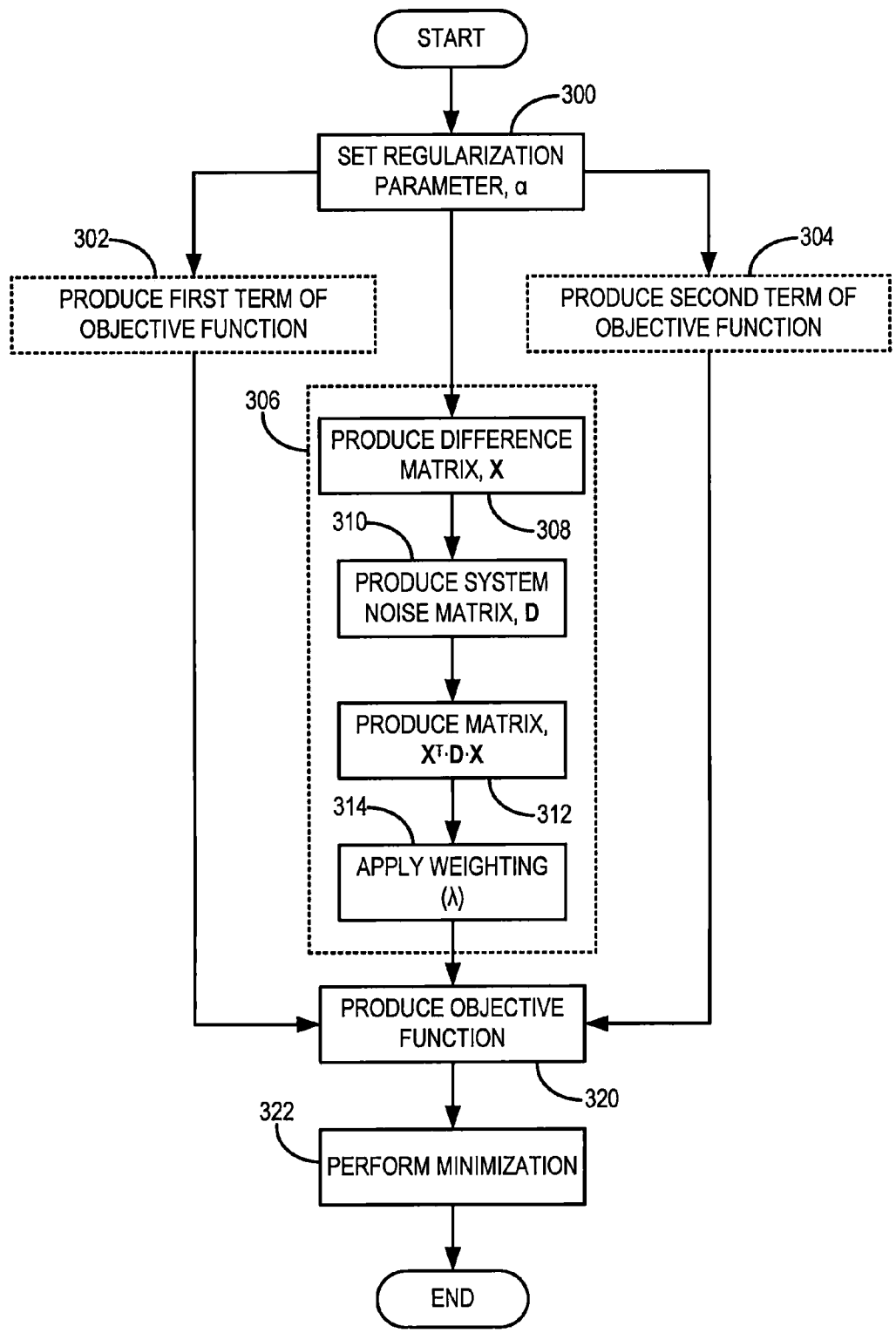
FIG. 3 is a flowchart setting forth the steps of yet another exemplary prior image constrained compressed sensing ("PICCS") image reconstruction method employed when practicing the present invention.

With reference now to FIG. 3, yet another implementation of the method of the present invention employs the objective function of Eqn. (12), and begins by initializing the regularization parameter, α, as indicated at step 300. Subsequently, the first and second terms in the objective function of Eqn. (12) are initialized, as indicated in steps 302 and 304, respectively. This process proceeds in the same manner as described above with reference to steps 102 and 104 in FIG. 1. Now, however, the consistency condition of Eqn. (3) and the effects of noise in the imaging system are incorporated into a third term, $\lambda(X^T D X)$, which is initialized at step 306. First, the difference matrix, X, is produced, as indicated at step 308, and described above with reference to step 208 in FIG. 2. Next, a system noise matrix, D, is produced, as indicated in step 310. The system noise matrix, D, is a diagonal matrix having matrix elements determined in accordance with the following:

$$D_{ij} = \begin{cases} \frac{1}{\sigma_n^2} & \text{if } i = j \\ 0 & \text{if } i \neq j. \end{cases} \qquad \text{Eqn. (17)}$$

As described above, $\sigma_n^2$, is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. Alternatively, in an MR imaging system, the noise parameter, $\sigma_n^2$, is estimated noise variance in the $n^{th}$ receiver coil. After the system noise matrix, D, has been produced, the following matrix multiplication is performed:

$$X^T D X \quad \text{Eqn. (18);}$$

as indicated at step 312. The result of this operation is subsequently scaled by the Lagrange multiplier, as indicated at step 314. The objective function of Eqn. (12) is subsequently produced in step 320 by adding the first, second, and third terms together. This objective function is then minimized, as indicated at step 322, using, for example, a nonlinear conjugate gradient method. The minimization process proceeds until a stopping criterion is satisfied, as described above.

X-Ray Computed Tomography Imaging System

Figure 4A:
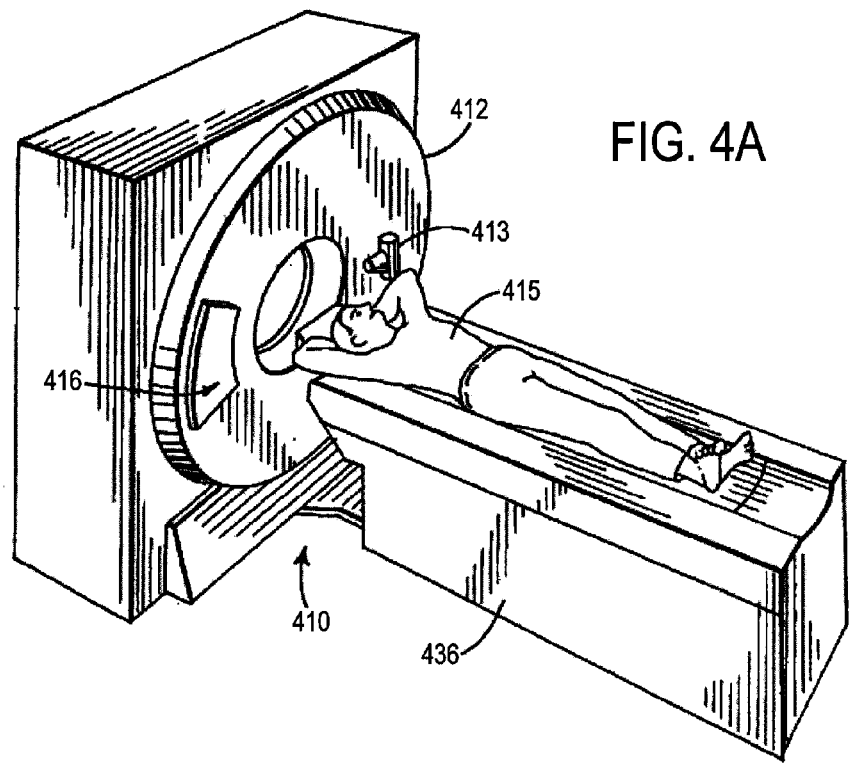
FIG. 4A is a pictorial view of an exemplary x-ray computed tomography ("CT") imaging system.
Figure 4B:
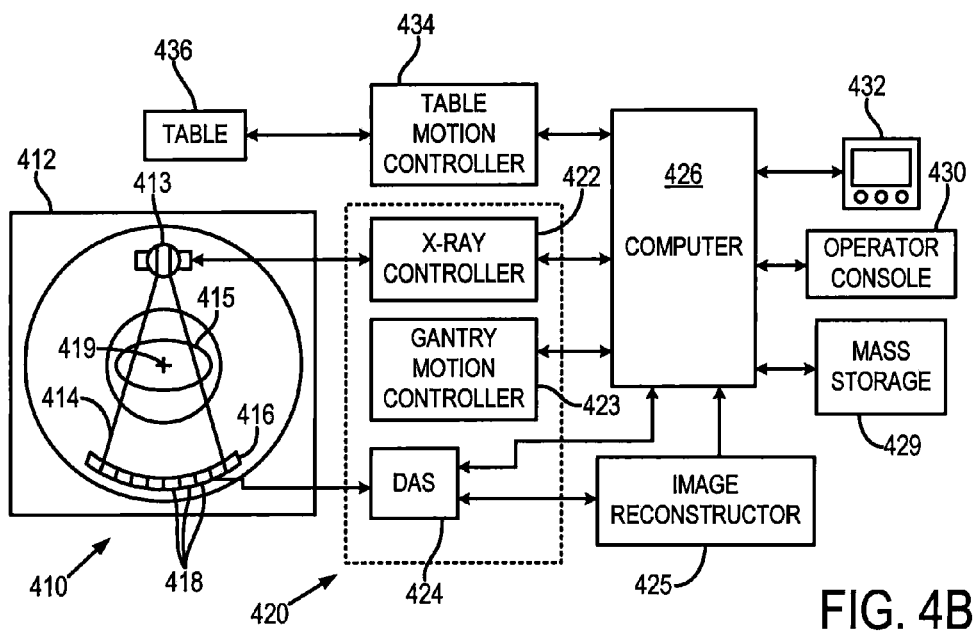
FIG. 4B is a block diagram of the CT imaging system of FIG. 4A.

With initial reference to FIGS. 4A and 4B, an x-ray computed tomography ("CT") imaging system 410 includes a gantry 412 representative of a "third generation" CT scanner. Gantry 412 has an x-ray source 413 that projects a fan-beam, or cone-beam, of x-rays 414 toward a detector array 416 on the opposite side of the gantry. The detector array 416 is formed by a number of detector elements 418 which together sense the projected x-rays that pass through a medical patient 415. Each detector element 418 produces an electrical signal that represents the intensity of an impinging x-ray beam and hence the attenuation of the beam as it passes through the patient. During a scan to acquire x-ray projection data, the gantry 412 and the components mounted thereon rotate about a center of rotation 419 located within the patient 415.

The rotation of the gantry and the operation of the x-ray source 413 are governed by a control mechanism 420 of the CT system. The control mechanism 420 includes an x-ray controller 422 that provides power and timing signals to the x-ray source 413 and a gantry motor controller 423 that controls the rotational speed and position of the gantry 412. A data acquisition system ("DAS") 424 in the control mechanism 420 samples analog data from detector elements 418 and converts the data to digital signals for subsequent processing. An image reconstructor 425, receives sampled and digitized x-ray data from the DAS 424 and performs high speed image reconstruction. The reconstructed image is applied as an input to a computer 426 which stores the image in a mass storage device 428.

The computer 426 also receives commands and scanning parameters from an operator via console 430 that has a keyboard. An associated display 432 allows the operator to observe the reconstructed image and other data from the computer 426. The operator supplied commands and parameters are used by the computer 426 to provide control signals and information to the DAS 424, the x-ray controller 422 and the gantry motor controller 423. In addition, computer 426 operates a table motor controller 434 which controls a motorized table 436 to position the patient 415 in the gantry 412.

C-Arm X-Ray Imaging System

Figure 5A:
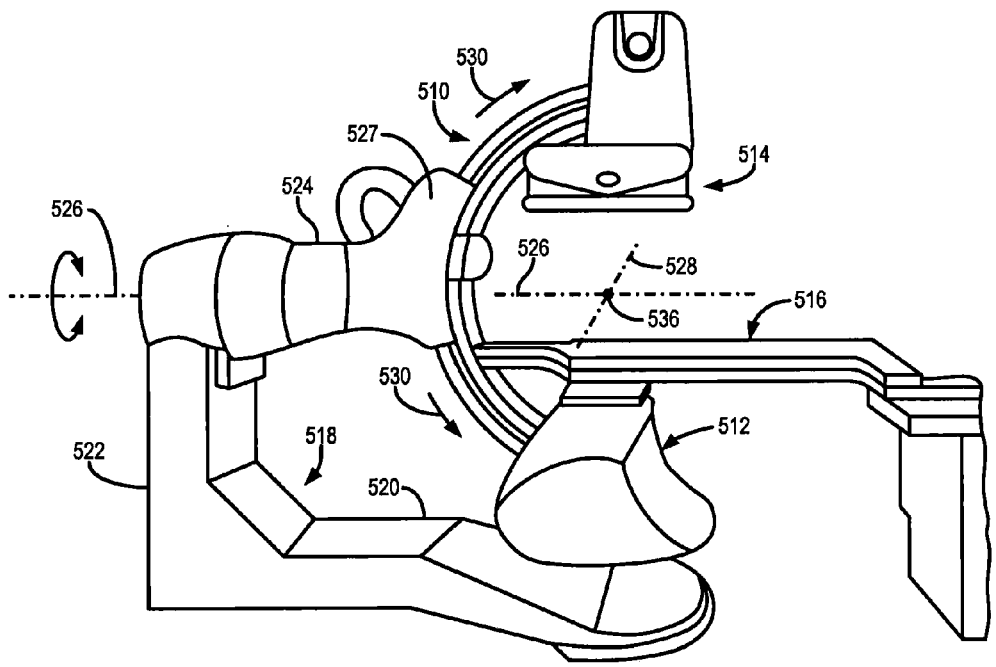
FIG. 5A is a pictorial view of an exemplary C-arm x-ray imaging system.
Figure 5B:
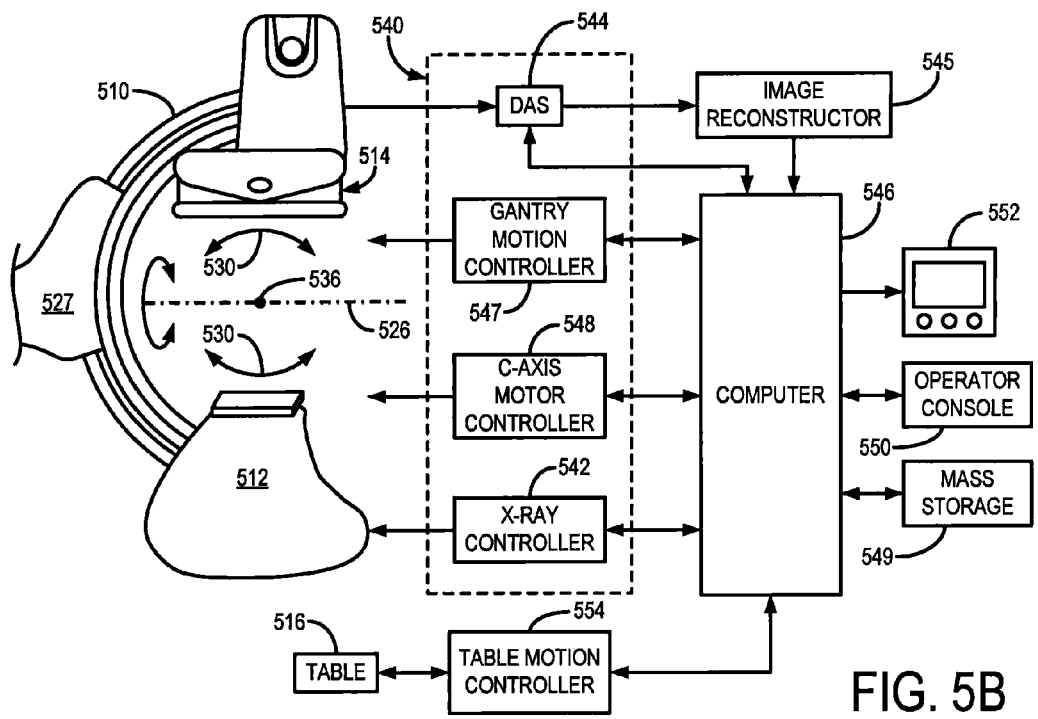
FIG. 5B is a block diagram of the C-arm x-ray imaging system of FIG. 5A.

Referring particularly to FIGS. 5A and 5B, an embodiment of the invention employs an x-ray system that is designed for use in connection with interventional procedures. It is characterized by a gantry having a C-arm 510 which carries an x-ray source assembly 512 on one of its ends and an x-ray detector array assembly 514 at its other end. The gantry enables the x-ray source 512 and detector 514 to be oriented in different positions and angles around a patient disposed on a table 516, while enabling a physician access to the patient.

The gantry includes an L-shaped pedestal 518 which has a horizontal leg 520 that extends beneath the table 516 and a vertical leg 522 that extends upward at the end of the horizontal leg 520 that is spaced from of the table 516. A support arm 524 is rotatably fastened to the upper end of vertical leg 522 for rotation about a horizontal pivot axis 526. The pivot axis 526 is aligned with the centerline of the table 516 and the arm 524 extends radially outward from the pivot axis 526 to support a C-arm drive assembly 527 on its outer end. The C-arm 510 is slidably fastened to the drive assembly 527 and is coupled to a drive motor (not shown) which slides the C-arm 510 to revolve it about a C-axis 528 as indicated by arrows 530. The pivot axis 526 and C-axis 528 intersect each other at an isocenter 536 located above the table 516 and they are perpendicular to each other.

The x-ray source assembly 512 is mounted to one end of the C-arm 510 and the detector array assembly 514 is mounted to its other end. As will be discussed in more detail below, the x-ray source 512 emits a cone beam of x-rays which are directed at the detector array 514. Both assemblies 512 and 514 extend radially inward to the pivot axis 526 such that the center ray of this cone beam passes through the system isocenter 536. The center ray of the cone beam can thus be rotated about the system isocenter around either the pivot axis 526 or the C-axis 528, or both during the acquisition of x-ray attenuation data from a subject placed on the table 516.

Figure 6A:
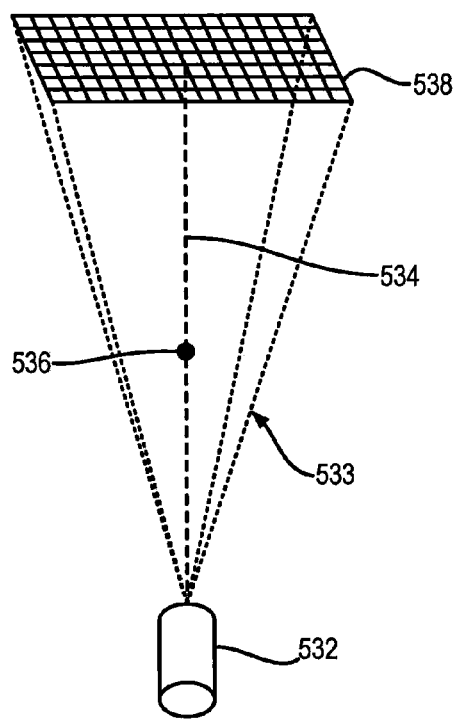
FIG. 6A is a pictorial view of the x-ray source and detector in the C-arm x-ray imaging system of FIG. 5A.

As shown in FIG. 6A, the x-ray source assembly 512 contains an x-ray source 532 which emits a cone beam 533 of x-rays when energized. The center ray 534 passes through the system isocenter 536 and impinges on a two-dimensional flat panel digital detector 538 housed in the detector assembly 514. Exemplary flat panel detectors 538 include so-called "small flat panel" detectors, in which the detector array panel 538 is around 20 cm by 20 cm in size. Such a detector panel allows the coverage of a field-of-view of around 12 cm. Each element produces an electrical signal that represents the intensity of an impinging x-ray and hence the attenuation of the x-ray as it passes through the patient. During a scan the x-ray source 532 and detector array 538 are rotated about the system isocenter 536 to acquire x-ray attenuation projection data from different angles. The detector array is able to acquire 30 projections, or views, per second and this is the limiting factor that determines how many views can be acquired for a prescribed scan path and speed.

Figure 6B:
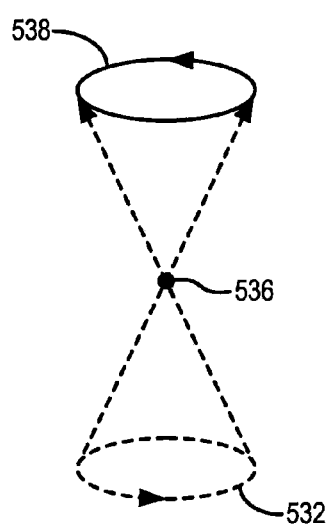
FIG. 6B is a pictorial view of the C-arm scan path employed by the C-arm x-ray imaging system of FIG. 5A.

Referring particularly to FIG. 6B, the rotation of the assemblies 512 and 514 and the operation of the x-ray source 532 are governed by a control mechanism 540 of the CT system. The control mechanism 540 includes an x-ray controller 542 that provides power and timing signals to the x-ray source 532. A data acquisition system ("DAS") 544 in the control mechanism 540 samples data from detector elements 538 and passes the data to an image reconstructor 545. The image reconstructor 545, receives digitized x-ray data from the DAS 544 and performs high speed image reconstruction according to the methods of the present invention. The reconstructed image is applied as an input to a computer 546 which stores the image in a mass storage device 549 or processes the image further.

The control mechanism 540 also includes pivot motor controller 547 and a C-axis motor controller 548. In response to motion commands from the computer 546 the motor controllers 547 and 548 provide power to motors in the x-ray system that produce the rotations about respective pivot axis 526 and C-axis 528. A program executed by the computer 546 generates motion commands to the motor drives 547 and 548 to move the assemblies 512 and 514 in a prescribed scan path.

The computer 546 also receives commands and scanning parameters from an operator via console 550 that has a keyboard and other manually operable controls. An associated cathode ray tube display 552 allows the operator to observe the reconstructed image and other data from the computer 546. The operator supplied commands are used by the computer 546 under the direction of stored programs to provide control signals and information to the DAS 544, the x-ray controller 542 and the motor controllers 547 and 548. In addition, computer 546 operates a table motor controller 554 which controls the motorized table 516 to position the patient with respect to the system isocenter 536.

Figure 7A:
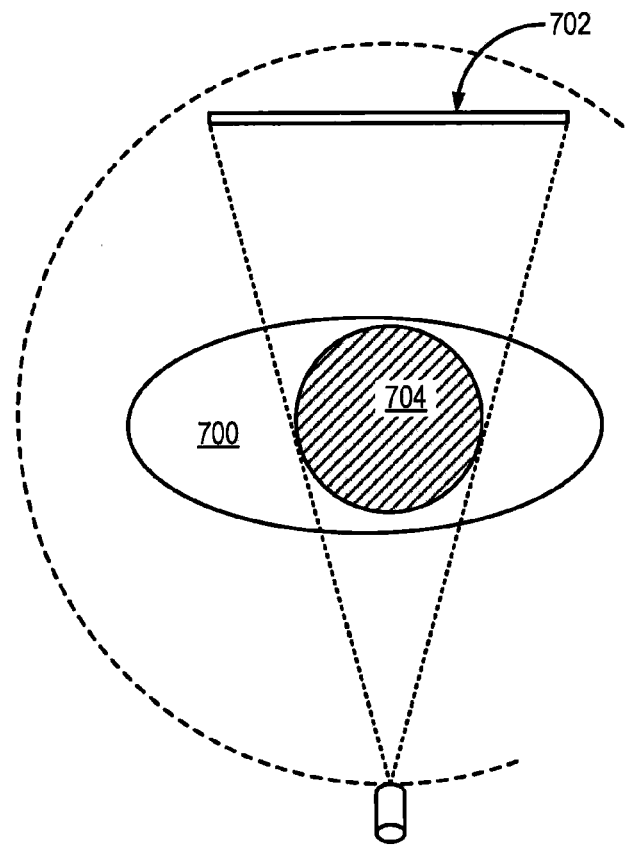
FIG. 7A is a pictorial view of a small flat-panel detector and the limited field-of-view associated with such a detector.
Figure 7B:
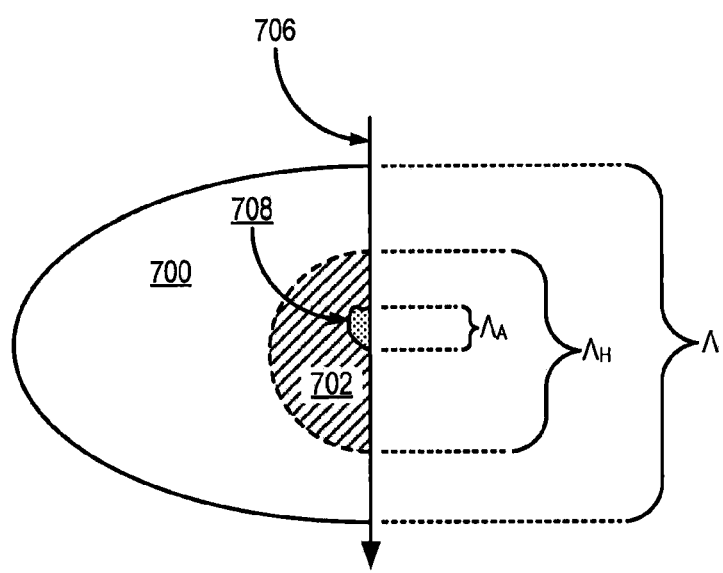
FIG. 7B is a pictorial view of an exemplary reconstruction line, $\Lambda$, passing through a subject and the portions of that reconstruction line corresponding to a region of known material, $\Lambda_A$, such as air, and to the limited field-of-view resulting from the use of a small flat-panel detector, $\Lambda_H$.

By way of example, and referring now to FIG. 7A, when a subject 700 is positioned in a C-arm x-ray imaging system that utilizes a small flat-panel 702, such as those described above, projection data is acquired only over a limited field-of-view 704. As a result, a method for producing a prior image and reconstructing a desired image of, for example, a cardiac phase of the subject's heart that both account for the truncated projection data is required. The succeeding description provides such methods. By way of further example, and referring now to FIG. 7B, a reconstruction line 706, $\Lambda$, along which projection data is acquired passes through the subject 700. More particularly, the reconstruction line 706 includes a portion that passes through the limited field-of-view 704, $\Lambda_H$, and a portion that passes through a region 708 in the subject with a known attenuation value, $\Lambda_A$, such as an air pocket. Using this knowledge, a prior image can be produced in an iterative manner by analyzing each line of projection data individually, and then combining the results, as will be described in detail below.

Image Reconstruction

Figure 8:
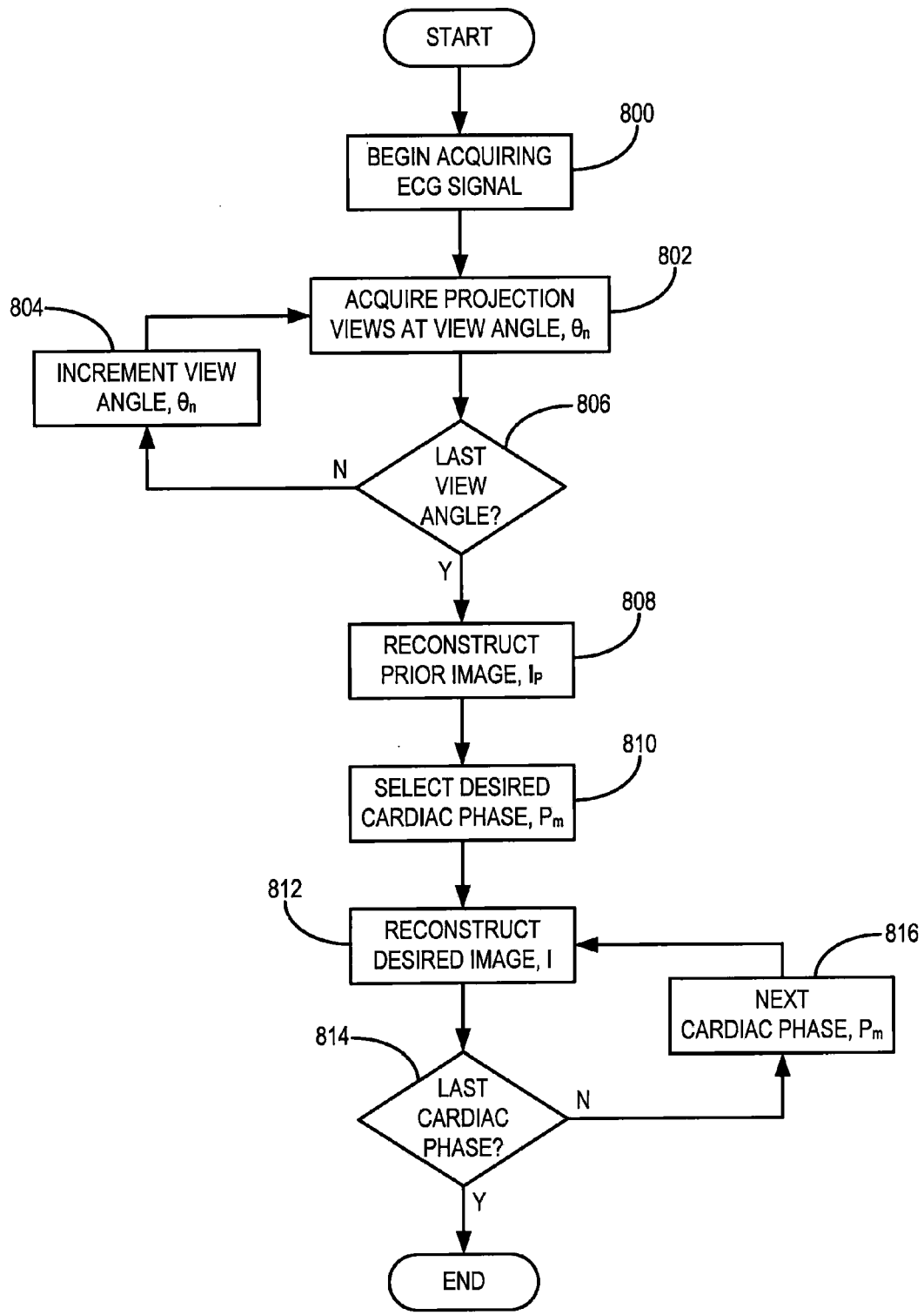
FIG. 8 is a flowchart setting forth the steps of a method in accordance with the present invention as performed by the CT imaging system of FIG. 5A or the C-arm x-ray imaging system of FIG. 6A.

An x-ray CT imaging system, such as the one described above with reference to FIGS. 4A and 4B, or an x-ray C-arm imaging system, such as the one described above with reference to FIGS. 5A and 5B can be employed to acquire image data in accordance with an embodiment of the present invention. Referring now particularly to FIG. 8, a flowchart setting forth the steps of an image reconstruction method in accordance with the present invention is illustrated. The method begins with the acquisition of an electrocardiogram ("ECG") signal from the subject, as indicated at step 800. This ECG signal is later used to retrospectively gate the acquired image data into M different cardiac phases, $P_M$. Data acquisition subsequently begins by acquiring image data in the form of a set of projection views at a first view angle, $\theta_n$, as indicated at step 802. The x-ray source and detectors are subsequently rotated to a new view angle at step 804, where image data is again acquired. This process is repeated until the x-ray source and detectors have been rotated to a last view angle, $\theta_N$, as indicated by decision block 806. After all of the desired image data has been acquired, the acquisition of the ECG signal is stopped.

After all of the image data has been acquired, the reconstruction process begins. First, a prior image, $I_P$, is reconstructed at step 808. In general, the prior image is reconstructed using a method that iteratively reconstructs the image as a series of reconstruction lines. For example, instead of having conventional image pixels that are reconstructed and rendered as squares, the reconstructed image has pixels that are reconstructed as lines, which are herein referred to as "reconstruction lines." As will be described below in detail with respect to FIG. 9, this method provides a suitable prior image, $I_P$, even from truncated projection data acquired with a small flat-panel detector.

Referring still to FIG. 8, the acquired image data is subsequently gated, retrospectively, into the M different cardiac phases, $P_m$, as described above in detail. This retrospective gating produces a "cardiac phase image data set" for each of the M different desired cardiac phases. Therefore, each cardiac phase image data set includes a plurality of projection views acquired during the gating window, $W_m$, corresponding to a given cardiac phase, $P_m$. In the alternative, the original image data acquisition can be prospectively gated such that image data is only acquired at specific time points during the ECG signal. Following this data acquisition scheme, all of the image data acquired during a selected cardiac phase is similarly combined into a cardiac phase image data set.

Since each cardiac phase image data set is highly undersampled and truncated, an attempt to reconstruct images using standard image reconstruction algorithms, such as the well-known filtered backprojection ("FBP") method, will result in severe streaking artifacts and distortion artifacts. Proceeding with the image reconstruction method, a first cardiac phase, $P_m$, is selected at step 810. As indicated next at step 812, a desired image, I, of the selected cardiac phase, $P_m$, is subsequently reconstructed using a method that utilizes, in part, the reconstruction methods described above with reference to FIGS. 1, 2, and 3. As will be described below in detail with reference to FIG. 10, a desired image, I, for each cardiac phase is reconstructed in a manner similar to the production of the prior image, $I_P$, above in step 808. Referring still to FIG. 8, a desired image, I, is reconstructed for each cardiac phase, $P_m$, in this manner until an image for each of the desired cardiac phases has been reconstructed, as decided at process block 814. If all of the desired images have not been reconstructed, a next cardiac phase, $P_m$, is selected at step 816 and the above described image reconstruction method is repeated.

Figure 9A:
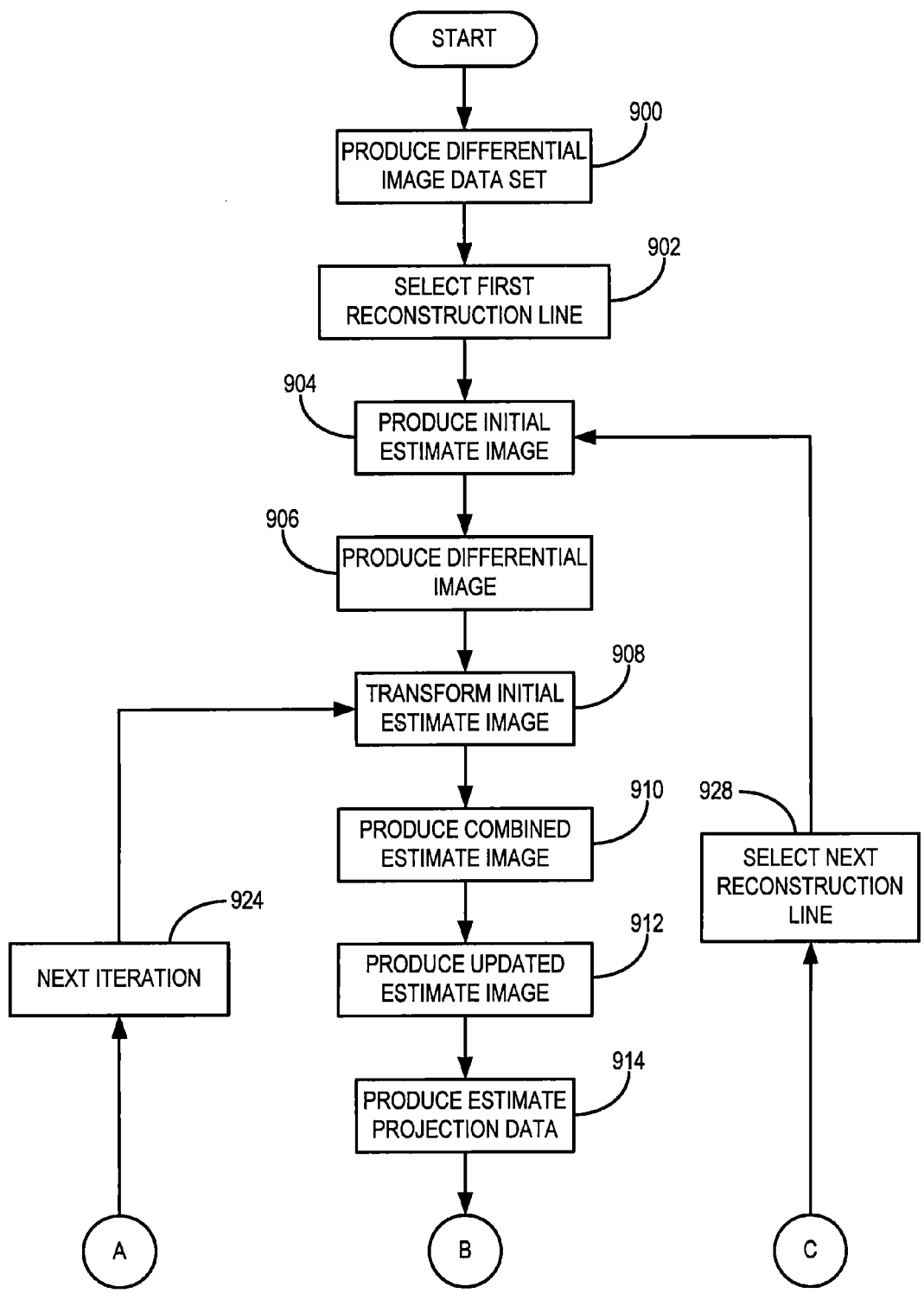
FIGS. 9A and 9B are flowcharts setting forth the steps of a method for reconstructing a prior image in accordance with the present invention.
Figure 9B:
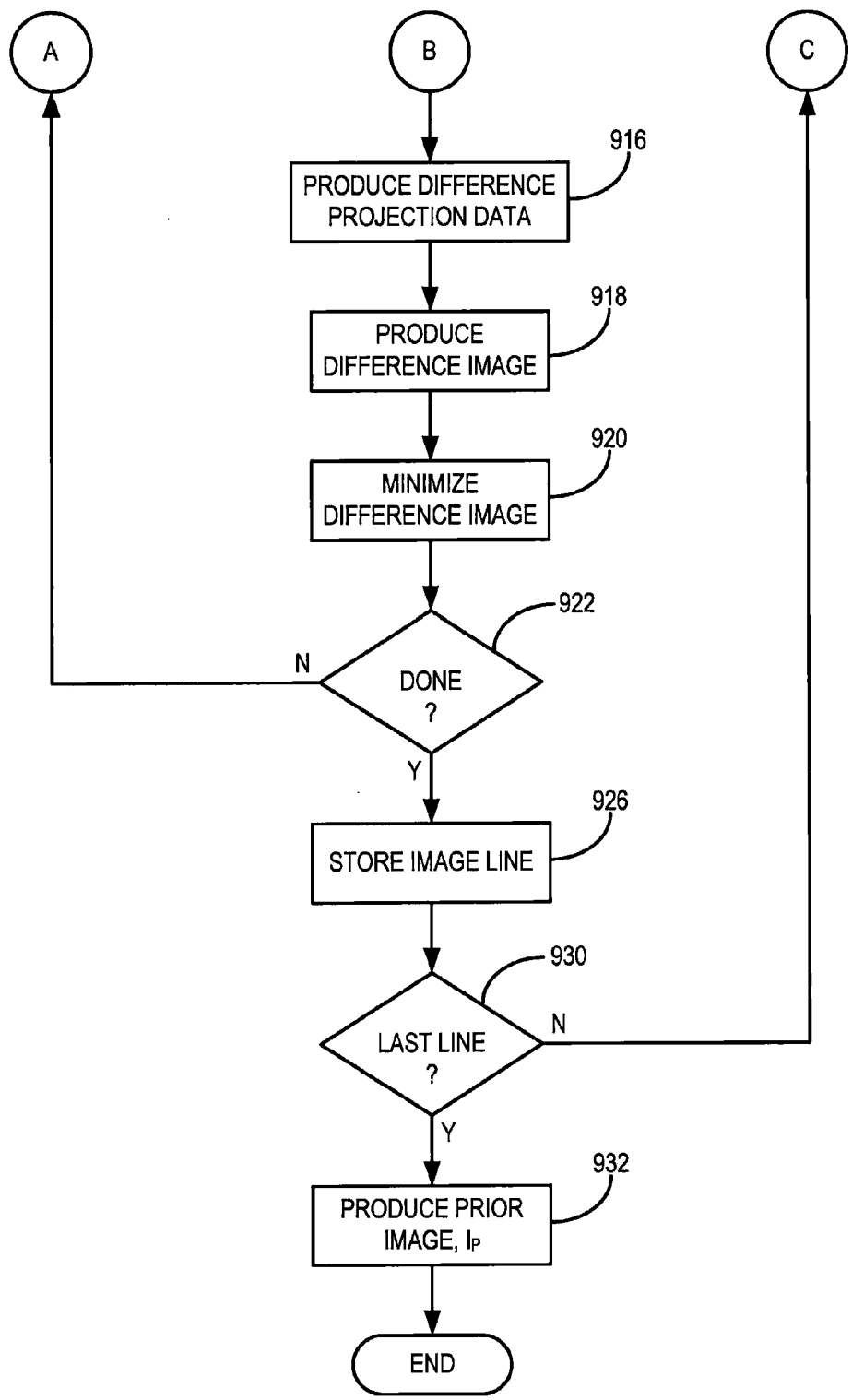

Referring now to FIGS. 9A and 9B, a flowchart setting forth the steps of a method for producing a prior image, $I_P$, of the subject in accordance with the present invention is illustrated. First, a differential projection data set is produced from the acquired image data, as indicated at step 900. An exemplary method for producing a differential projection data set is described, for example, in U.S. Pat. No. 7,251,307, which is herein incorporated by reference. In general, however, when a flat-panel detector is utilized to detect attenuated x-rays, the differential projection data, $g_d$, is calculated in terms of the detector coordinates, u, v, and the source parameter, t. Namely, the differential projection data is given by:

$$g_d(u, v, t) = \left(\frac{D^2 + u^2}{D} \cdot \frac{\partial}{\partial u} + \frac{uv}{D} \cdot \frac{\partial}{\partial v} - \frac{\partial}{\partial t}\right) \cdot g(u, v, t); \quad \text{Eqn. (19)}$$

where D is the distance from the x-ray source to the detector iso-center, and g is the acquired projection data.

After the differential projection data has been produced, a first reconstruction line, $\Lambda$, is selected for processing, as indicated at step 902. For a given reconstruction line, $\Lambda$, passing through a small region of interest where the CT number is known a priori, an iterative process is performed on the reconstruction line, $\Lambda$, to reconstruct image pixel values of the pixels on the line. The reconstruction process begins by producing an initial estimate image, $f_0(x)^{(k)}$, of the reconstructed reconstruction line, Λ, as indicated at step 904. In general, the initial estimate image, $f_0(x)^{(k)}$, has the following form:

$$f_0(x)^{(k)} = \begin{cases} 0 & x \in \Lambda \setminus \Lambda_A \\ -1000 & x \in \Lambda_A, \end{cases}$$

where Λ is the reconstruction line; $\Lambda_A$ is the portion of the reconstruction line that passes through a region in the subject that is substantially air, which has a Hounsfield unit ("HU") of −1000, or substantially lung tissue, which has an average HU of −800; and $x \in \Lambda \setminus \Lambda_A$ indicates those values in the reconstruction line Λ that are not in the portion passing through air, $\Lambda_A$. It is noted that the initial estimate image includes image intensity values for the line in the resultant image matrix that is associated with the selected reconstruction line, Λ. Next, the differential projection data set is backprojected onto the corresponding reconstruction line Λ to obtain a differential image, DBP(x), as indicated at step 906. It is noted, however, that because of the truncation that occurs with the small flat-panel detector, only the portion of the reconstruction line, Λ, that passes through the scan field-of-view ("FOV"), $\Lambda_H$, is backprojected. Subsequently, the initial estimate image, $f_0(x)^{(k)}$, is transformed, as indicated at step 908. For example, the initial estimate image, $f_0(x)^{(k)}$, is transformed using a Hilbert transform to produce a transformed initial estimate image, Hf(x).

After the transformed initial estimate image, Hf(x), is produced, a combined estimate image, MHf(x), is produced as indicated at step 910. The combined estimate image, MHf(x), is produced by combining the transformed initial estimate image, Hf(x), and the backprojected differential projection, DBP(x), as follows:

$$MHf(x) = \begin{cases} Hf(x) & x \in \Lambda \setminus \Lambda_H \\ DBP(x) & x \in \Lambda_H; \end{cases} \quad \text{Eqn. (20)}$$

where $x \in \Lambda \setminus \Lambda_H$ indicates those values in the reconstruction line, Λ, that are not in the portion passing through the scan FOV, $\Lambda_H$. Following this step, an updated estimate image, $f_1(x)^{(k)}$, of the reconstructed reconstruction line, Λ, is produced, as indicated at step 912. For example, the updated estimate image, $f_1(x)^{(k)}$, is produced by calculating the inverse Hilbert transform of the combined estimate image, MHf(x).

A loop is now entered, in which the reconstructed reconstruction line, Λ, is iteratively estimated. First, the updated estimate image, $f_1(x)^{(k)}$, is forward projected in order to produce estimate projection data, as indicated at step 914. The estimate projection data is then subtracted from the acquired image data in order to produce difference projection data, as indicated at step 916. The result of this difference is backprojected onto the reconstruction line, Λ, to produce a difference image, as indicated at step 918, that is then minimized, as indicated at step 920. For example, the difference image is minimized using a convex optimization method that is constrained using the consistency condition of Eqn. (3), as well as the assumption that the attenuation coefficient is positive, which is referred to as a positivity constraint. A determination is then made at decision block 922 whether this minimized difference image satisfies a stopping criterion, such as the stopping criterion in Eqn. (15). If not, the minimized difference image is selected as the initial estimate image for a next iteration, as indicated at step 924. Steps 908-920 are then repeated and the determination again made at decision block 922 as to whether the stopping criterion has been met.

When the stopping criterion has been reached, the minimized difference image is stored as an "image line," as indicated at step 926, and the entire process repeated for the next reconstruction line, as indicated at step 928. After all of the individual reconstruction lines have been processed in this manner, as decided at decision block 930, the corresponding image lines are combined to produce the prior image, $I_P$, as indicated at step 932. For example, each reconstruction line corresponds to one row or column of the image matrix for the prior image, $I_P$. Accordingly, the prior image, $I_P$, is produced by forming a full image matrix by appropriately combining the individually reconstructed image lines.

Figure 10A:
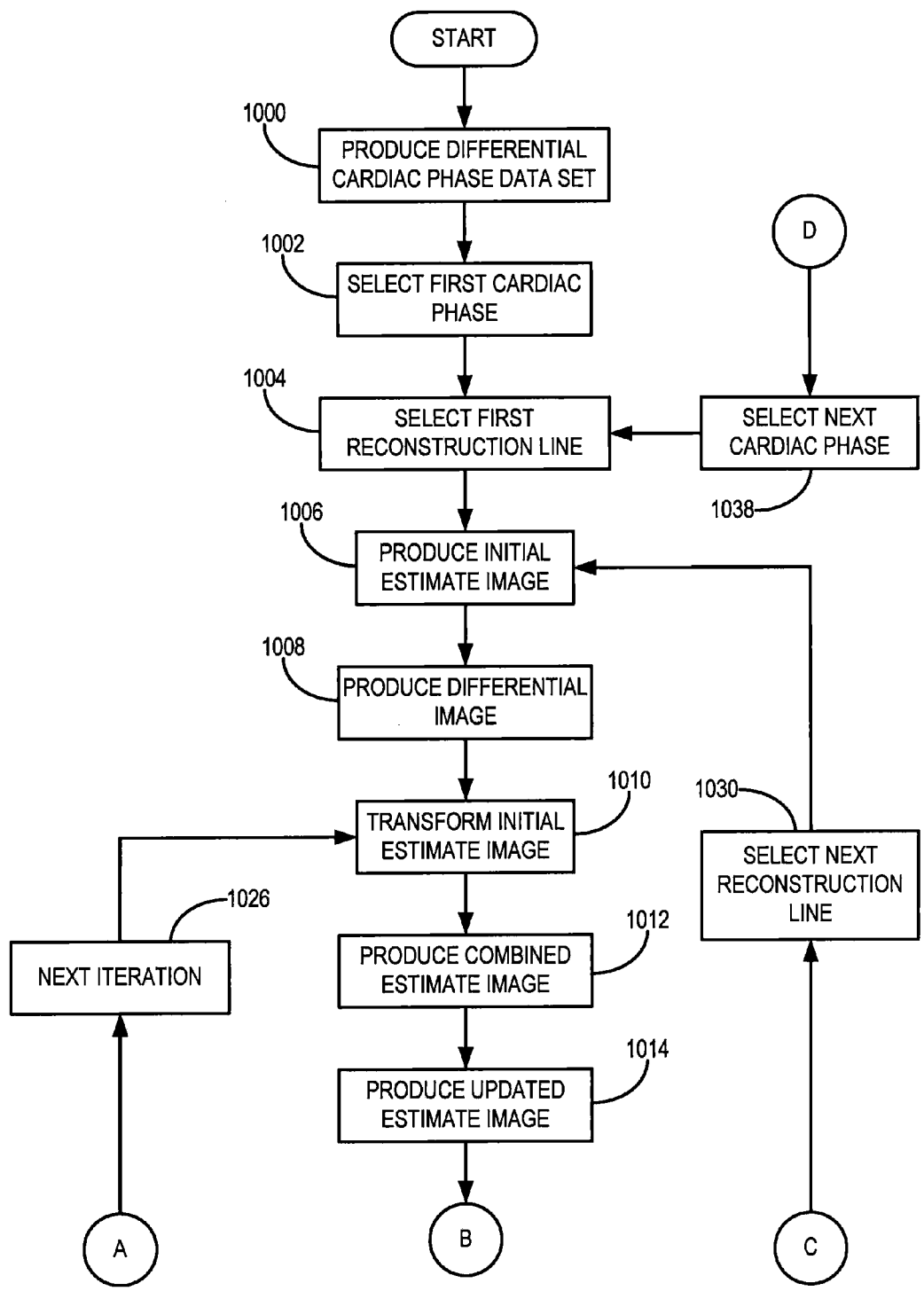
FIGS. 10A and 10B are flowcharts setting forth the steps of a method for reconstructing a cardiac phase image in accordance with the present invention.
Figure 10B:
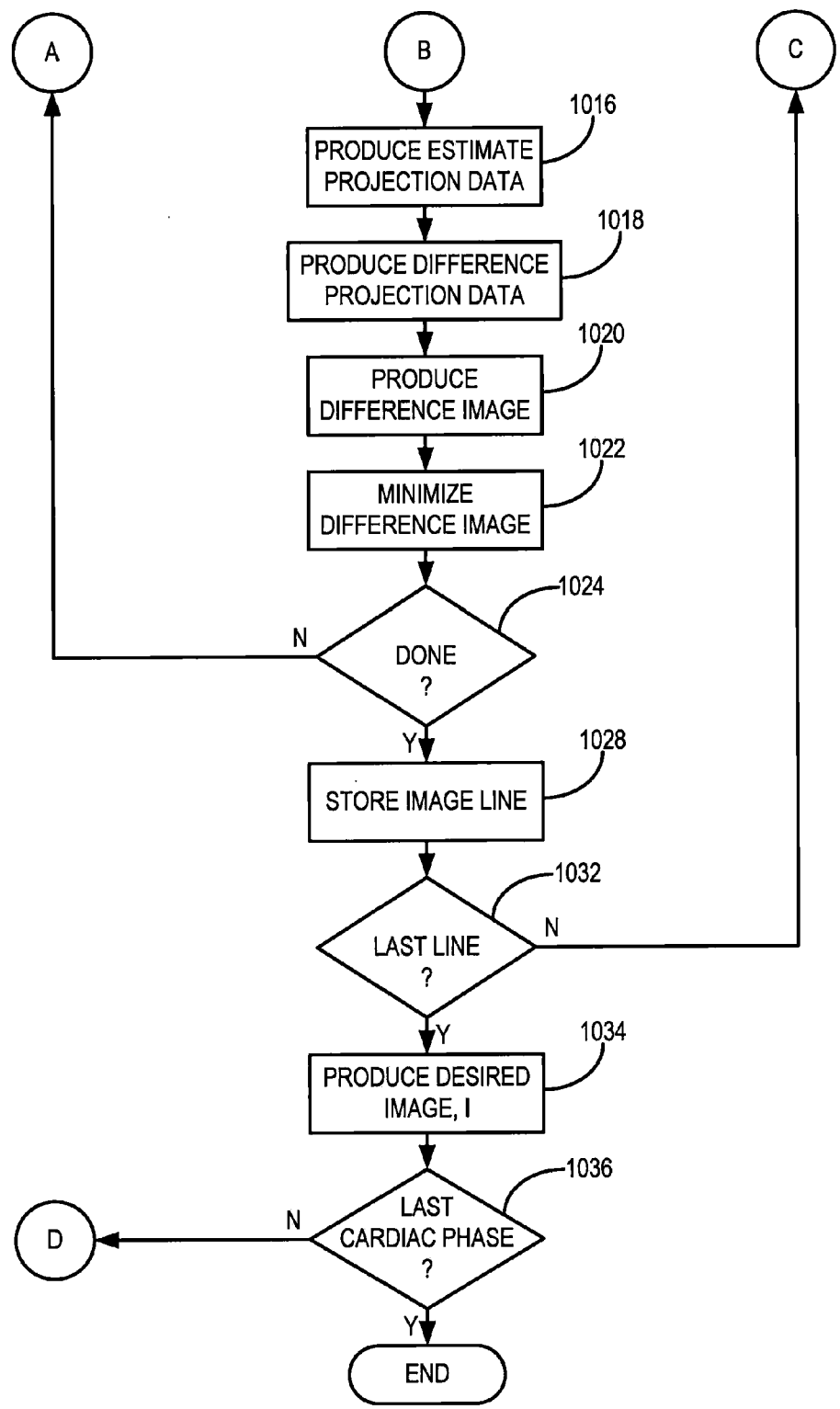

Referring now to FIGS. 10A and 10B, a flowchart setting forth the steps of an exemplary image reconstruction method that utilizes a prior image, $I_P$, produced in accordance with the present invention is illustrated. Similar to the above-described method for producing a prior image, $I_P$, a differential cardiac phase projection data set is first produced from the selected cardiac phase image data set, as indicated at step 1000. In general, the available data for a specific cardiac phase is very limited. For example, only about 10 projection view angles may be included in a given cardiac phase image data set. Therefore, some projections from other cardiac phases are included in the differential cardiac phase projection data set without substantially contaminating the temporal information. To achieve this, a "sliding window" type weighting function is utilized. Namely, if data belongs to selected target cardiac phase, a weight of one is attributed to that data. On the other hand, for other neighboring cardiac phases, a smaller weight is assigned. The farther away in time the data lies from the selected cardiac phase, the smaller the weight that is given to that data.

A first cardiac phase is selected for processing, as indicated at step 1002. For each line in the image matrix for each desired cardiac phase image, an iterative minimization process is performed in a similar manner to the method employed to produce the prior image, $I_P$. Thus, a first reconstruction is selected, as indicated at step 1004. Then, an initial estimate image, $f_0(x)^{(k)}$, is produced, as indicated at step 1006, using the prior image, $I_P$, as follows:

$$f_0(x)^{(k)} = \begin{cases} I_P(x) & x \in \Lambda \setminus \Lambda_A \\ -1000 & x \in \Lambda_A. \end{cases} \quad \text{Eqn. (21)}$$

where Λ is the reconstruction line; $\Lambda_A$ is the portion of the reconstruction line that passes through a region in the subject that is substantially air, which has a Hounsfield unit ("HU") of −1000; and $x \in \Lambda \setminus \Lambda_A$ indicates those values in the reconstruction line Λ that are not in the portion passing through air, $\Lambda_A$. Next, the differential cardiac phase projection data set is backprojected onto the corresponding reconstruction line Λ to obtain a differential image, DBP(x), as indicated at step 1008. It is noted, however, that because of the truncation that occurs with the small flat-panel detector, only the portion of the reconstruction line, Λ, that passes through the scan field-of-view ("FOV"), $\Lambda_H$, is backprojected. Subsequently, the initial estimate image, $f_0(x)^{(k)}$, is transformed, as indicated at step 1010. For example, the initial estimate image, $f_0(x)^{(k)}$, is transformed using a Hilbert transform to produce a transformed initial estimate image, Hf(x).

After the transformed initial estimate image, Hf(x), is produced, a combined estimate image, MHf(x), is produced as indicated at step 1012. The combined estimate image, MHf(x), is produced by combining the transformed initial estimate image, Hf(x), and the backprojected differential projection, DBP(x), as follows:

$$MHf(x) = \begin{cases} Hf(x) & x \in \Lambda \setminus \Lambda_H \\ DBP(x) & x \in \Lambda_H; \end{cases} \quad \text{Eqn. (22)}$$

where $x \in \Lambda \setminus \Lambda_H$ indicates those values in the reconstruction line, $\Lambda$, that are not in the portion passing through the scan FOV, $\Lambda_H$. Following this step, an updated estimate image, $f_1(x)^{(k)}$, of the reconstructed reconstruction line, $\Lambda$, is produced, as indicated at step 1014. For example, the updated estimate image, $f_1(x)^{(k)}$, is produced by calculating the inverse Hilbert transform of the combined estimate image, MHf(x).

A loop is now entered, in which the reconstructed reconstruction line, $\Lambda$, is iteratively estimated. First, the updated estimate image, $f_1(x)^{(k)}$, is forward projected in order to produce estimate projection data, as indicated at step 1016. The estimate projection data is then subtracted from the corresponding acquired image data associated with the given cardiac phase in order to produce difference projection data, as indicated at step 1018. The result of this difference is backprojected onto the reconstruction line, $\Lambda$, in order to produce a difference image, as indicated at step 1020, which is then minimized, as indicated at step 1022. This minimization is a two step process. For example, first the difference image is minimized using a convex optimization method that is constrained using the consistency condition of Eqn. (3), as well as the assumption that the attenuation coefficient is positive, which is referred to as a positivity constraint. However, after this minimization a second minimization process is performed using the prior image, $I_P$, produced earlier. In general, the second minimization includes the performance of a prior image constrained compressed sensing ("PICCS") method, such as those described in detail above with respect to FIGS. 1, 2, and 3. A determination is then made at decision block 1024 whether this minimized difference image satisfies a stopping criterion, such as the stopping criterion in Eqn. (15). If not, the minimized difference image is selected as the initial estimate image for a next iteration, as indicated at step 1026. Steps 1010-1022 are then repeated and the determination again made at decision block 1024 as to whether the stopping criterion has been met.

When the stopping criterion has been reached, the minimized difference image is stored as an "image line," as indicated at step 1028, and the entire process repeated for the next reconstruction line, as indicated at step 1030. After all of the individual reconstruction lines have been processed in this manner, as decided at decision block 1032, the corresponding projection images are combined to produce the desired image of the selected cardiac phase, I, as indicated at step 1034. A determination is then made at decision block 1036 as to whether images for all of the desired cardiac phases have been reconstructed. If not, then the next cardiac phase is selected at step 1038, and steps 1004-1034 are repeated to produce a desired image, I, for the newly selected cardiac phase.

It should be appreciated by those skilled in the art that for the above described image reconstruction method, many equivalents, alternatives, variations, and modifications, aside from those expressly stated, are possible and within the scope of the invention. For example, the subject's respiration can be monitored with a respiration monitoring device, such as a respiratory belt, and image data retrospectively gated based on the measured respiratory information. In this manner, motion, such as internal organ motion, can be compensated for when reconstructing images.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a subject with an x-ray imaging system, the method comprising the steps of:
    a) acquiring, with the x-ray imaging system, an image data set along a series of projection views at each of a plurality of projection view angles;
    b) producing a prior image of the subject by reconstructing each line in an corresponding image matrix using an iterative estimation process in order to form a prior image in which truncation artifacts are substantially suppressed;
    c) selecting an estimate image of the subject;
    d) producing a sparsified image of the subject using the prior image and the estimate image; and
    e) reconstructing a desired image of the subject using the sparsified image, the estimate image, and the acquired image data set.

2. The method as recited in claim 1 in which step b) includes producing an initial image estimate for each line in the image matrix by:
    i) setting each image intensity value in a portion of each initial image estimate associated with a selected material and disposed along the corresponding line in the image matrix to a known attenuation value; and
    ii) setting each image intensity value in each initial image estimate not associated with the selected material to zero.

3. The method as recited in claim 2 in which step b) further includes:
    iii) producing a differential image data set from the acquired image data set;
    iv) producing a differential image for each line in the image matrix set using the produced differential image data set;
    v) producing a combined image for each line in the image matrix by combining the corresponding initial estimate image and the differential image;
    vi) producing a difference image corresponding to each line in the image matrix using the corresponding produced combined image and the acquired image data;
    vii) minimizing each difference image subject to a consistency condition; and
    viii) combining each minimized difference image to produce the prior image.

4. A method for producing an image of a subject with an x-ray imaging system, the method comprising the steps of:
    a) acquiring, with the x-ray imaging system, an image data set along a series of projection views at each of a plurality of projection view angles;
    b) producing a prior image of the subject by:
        i) producing a differential image data set from the acquired image data set;
        ii) producing an initial estimate image for each line in an image matrix;
        iii) producing a differential image for each line in the image matrix set using the produced differential image data set;
        iv) producing a combined image for each line in the image matrix by combining the corresponding initial estimate image and the differential image;

v) producing a difference image corresponding to each line in the image matrix using the corresponding produced combined image and the acquired image data;

vi) minimizing each difference image subject to a consistency condition;

vii) combining each minimized difference image to produce the prior image;

c) selecting an estimate image of the subject;

d) producing a sparsified image of the subject using the prior image and the estimate image; and e) reconstructing a desired image of the subject using the sparsified image, the estimate image, and the acquired image data set.

5. The method as recited in claim 4 in which step b) ii) includes setting each image intensity value in the initial estimate image associated with a selected material disposed along the corresponding line in the image matrix to a known attenuation value and setting each image intensity value in the initial estimate image not associated with the selected material to zero.

6. The method as recited in claim 5 in which the selected material is air and the known attenuation value is approximately −1000 Hounsfield units.

7. The method as recited in claim 5 in which the selected material is lung tissue and the known attenuation value is around −800 Hounsfield units.

8. The method as recited in claim 4 in which step b) iv) includes performing a Hilbert transform on each initial estimate image before performing the combination.

9. The method as recited in claim 4 in which step b) v) includes:

performing an inverse Hilbert transform on each combined image;

producing a plurality of projection estimate data by forward projecting each transformed combined image;

producing a plurality of difference projection data by subtracting each of the plurality of projection estimate data from the corresponding acquired image data; and reconstructing a difference image for each line in the image matrix from each of the corresponding plurality of difference projection data.

10. The method as recited in claim 4 in which each minimized difference image corresponds to a different line in the image matrix, and step b) vii) includes producing the prior image by forming a prior image matrix from the minimized difference images.

11. The method as recited in claim 4 in which step a) further includes acquiring an electrocardiogram (ECG) signal from the subject and correlating the image data set with the ECG signal is acquired and step e) includes reconstructing an image of the subject's heart.

12. The method as recited in claim 11 in which steps c) e) are repeated to produce a plurality of images, each of the plurality of images being indicative of a different cardiac phase of the subject's heart.

13. The method as recited in claim 12 in which step c) includes:

i) producing a plurality of cardiac phase data sets using the acquired ECG signal and the acquired image data set;

ii) producing a plurality of differential cardiac phase data sets from the plurality of cardiac phase data sets;

iii) producing an initial estimate image for each line in each of a plurality of image matrices corresponding to each of a respective plurality of cardiac phases;

iv) producing a differential image for each line in each of the plurality of image matrices using the produced plurality of differential cardiac phase data sets;

v) producing a combined image for each line in each of the plurality of image matrices by combining the corresponding initial estimate image and differential image;

vi) producing a difference image corresponding to each line in each of the plurality of image matrices using the corresponding produced combined image and image data associated with the projection view;

vii) minimizing each difference image subject to a consistency condition; and viii) combining each minimized difference image to produce the estimate image.

14. The method as recited in claim 13 in which step c) iii) includes setting each image intensity value in the initial estimate image associated with a selected material disposed along the corresponding line in the respective image matrix to a known attenuation value and setting each image intensity value in the initial estimate image not associated with the selected material to an image intensity value in a corresponding line in the produced prior image.

15. The method as recited in claim 14 in which the selected material is air and the known attenuation value is around −1000 Hounsfield units.

16. The method as recited in claim 13 in which step c) v) includes performing a Hilbert transform on each initial estimate image before performing the combination.

17. The method as recited in claim 13 in which step c) vi) includes:

performing an inverse Hilbert transform on each combined image;

producing a plurality of projection estimate data by forward projecting each transformed combined image;

producing a plurality of difference projection data by subtracting each of the plurality of projection estimate data from the corresponding acquired image data; and reconstructing a difference image for each line in each of the plurality of image matrices from each of the corresponding plurality of difference projection data.

* * * * *